US00PP28713P2

(12) United States Plant Patent
Pavlich

(10) Patent No.: US PP28,713 P2
(45) Date of Patent: Nov. 28, 2017

(54) ***BEGONIA* PLANT NAMED 'TNBEGDY'**

(50) Latin Name: ***Begonia* hybrid**
Varietal Denomination: TNBEGDY

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/999,888

(22) Filed: Jul. 14, 2016

(51) Int. Cl.
*A01H 5/02* (2006.01)

(52) U.S. Cl.
USPC ..... Plt./343

(58) Field of Classification Search
USPC ..... Plt./343, 346
CPC ..... A01H 5/0238; A01H 5/02; A01H 5/00
See application file for complete search history.

(56) References Cited

PUBLICATIONS

Greenhouse Management Terra Nova Nurseries displays new varieties at 2016 California Spring Trials Apr. 8, 2016, retrieved on Aug. 15, 2017, retrieved from the Internet at http://www.greenhousemag.com/article/terra-nova-2016-trials/ 3 pp.*

Terra Nova Nurseries Professioanl Growers—*Begonia* Daystar Yellow 2017, retrieved on Aug. 15, 2017, retrieved from the Internet at http://www.terranovanurseries.com/growers/begoniadaystaryellow-p-818.html 2 pp.*

* cited by examiner

*Primary Examiner* — June Hwu
(74) *Attorney, Agent, or Firm* — Klarquist Sparkman, LLP

(57) ABSTRACT

A new and distinct form of *Begonia* plant characterized by attractive dark and patterned foliage, numerous large yellow flowers, continuous bloom time, a trailing habit, and excellent vigor.

1 Drawing Sheet

Botanical denomination: *Begonia* hybrid.
Variety designation: 'TNBEGDY'.

BACKGROUND OF THE INVENTION

The present invention relates to a new and distinct cultivar of *Begonia*, of the family Begoniaceae, and given the cultivar name, 'TNBEGDY'. *Begonia* 'TNBEGDY' is a tuberous Rex hybrid involving breeding lines using *Begonia* Rex, *Begonia tuberhybrida*, and *Begonia boliviensis*. The new cultivar originated from controlled cross of *Begonia* 'MY', as the seed parent, and *Begonia* B52-07, as the pollen parent. Both parents are proprietary seedlings.

This selection is uniquely characterized by:

1. attractive dark and patterned foliage,
2. numerous large yellow flowers,
3. continuous bloom time,
4. a trailing habit, and
5. excellent vigor.

Compared to *Begonia* 'Apricots and Lemons', an unpatented plant, the new cultivar has darker foliage and single rather than double flowers.

Compared to *Begonia* Bon Bon Series, unpatented plants using *Begonia boliviensis* breeding, the new cultivar has larger flowers and darker leaves.

The new variety has been reproduced only by asexual propagation (leaf and stem cuttings and tissue culture using growing tips). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 12 month old plant of the new cultivar in 10 inch pot in a warm greenhouse in April in full bloom in Canby, Oreg.

FIG. 2 shows a close up of the same plant.

DETAILED PLANT DESCRIPTION

The following is a detailed description of the new *Begonia* cultivar based on observations of 5- to 24-month-old specimens grown in 4 inch to one gallon containers in a warm greenhouse in April in Canby, Oreg. The color descriptions are all based on *The Royal Horticultural Society Colour Chart*, 5$^{th}$ edition, 2007.

Plant:

*Type*.—Herbaceous, rhizomatous perennial.
*Form*.—Upright when young, caulescent, becoming decumbent with maturity.
*Cold hardiness*.—USDA Zone 10.
*Size*.—Grows to 60 cm deep and 50 cm wide.
*Vigor*.—Excellent.
*Roots*.—Rooting initiates in two weeks, roots White NN155C in color.

Stem:

*Type*.—Upright in first weeks, becoming decumbent at about 6 weeks if given sufficient spacing.

*Size*.—Grows to 30 cm long and 1.5 mm wide.
*Internodes*.—From 1 cm to 3 cm long.
*Surface*.—Pubescent.
*Color*.—Greyed Purple 187A at nodes, dulling to Grey Brown 199B tinted Greyed Purple 187A between the nodes.

Leaf:
*Type*.—Simple.
*Arrangement*.—Alternate.
*Shape*.—Obliquely lanceolate, assymetric.
*Leaf strength*.—Good.
*Blade size*.—Grows to 6.5 cm wide and 17 cm long.
*Margins*.—Doubly serrate, sometimes slightly undulate, 0 to 1 side lobe.
*Apex*.—Acuminate.
*Base*.—Oblique and truncate.
*Venation*.—Palmate, Green 137A topside, bottom side Yellow Green 148B when grown cooler and shadier, Greyed Purple 187A on top and bottom side when grown in higher light or temperatures.
*Surface texture*.—Pubescent on both sides.
*Stipules*.—Deciduous, ovate, 9 mm long and 7 mm wide, apex acute, base clasping, entire, both sides pubescent and Greyed Purple 187B.
*Petiole description*.—Grows to 6 cm long and 4 mm wide, succulent, pubescent, Greyed Brown 199A heavily tinted Greyed Purple 187A.
*Leaf color*.—Top side between Greyed Purple N186A and Green 139A (with vein area lightened to Green 137A when it is cooler or shadier); bottom side Greyed Purple 187B (Red Purple 59A with vein area Yellow Green 148B when cooler or shadier).

Inflorescence:
*Type*.—Axillary, bisexual, cymose.
*Number of flowers per cyme*.—2 to 4.
*Peduncle description*.—Grows 5 cm long and 4 mm wide, pubescent, moderately strong, Greyed Red 178A; with 2 opposite, dehiscent petiolate leaf-bracts below each cyme, broadly ovate, grow to 10 mm wide and 12 mm long, margins ciliate, tip obtuse to notched, base clasping, both sides glabrous, both sides Yellow Green 145A lightly tinted Greyed Purple 187A on top margin.
*Pedicel description*.—Grow to 23 mm long, 2.5 mm wide, pubescent, medium strength, Greyed Yellow 161A (tinted Greyed Purple 187B in high light).
*Bloom period*.—Year round in Canby, Oreg.

Flower bud:
*Size*.—Staminate flower bud to 28 mm long and 25 mm wide, pistillate flower bud to 33 mm long and 20 mm wide.
*Shape*.—Flat oval.
*Surface texture*.—Glabrous.
*Color*.—Yellow 2C on top half blending to Green Yellow 1C on bottom, Yellow Green 144A on ovary.

Flower:
*Type*.—Monoecious, bilaterally symmetrical.
*Pistillate flower*.—Grows to 30 mm deep and 70 mm wide overall; 5 fleshy tepals, each grow to 31 mm long and 18 mm wide, obovate, tip obtuse to acute, base cuneate, margins entire to weakly undulate, glabrous on both sides, inside Yellow 8B, bottom side Yellow 9D (tinted Red Purple 59C on outer tepals in high light); 1 pistil, to 25 mm long overall, ovary to 28 mm wide and 15 mm deep, three winged (one short and 2 longer), Yellow Green 146C (tinted Red Purple 159C on wings in high light), style 3-branched, 5 mm deep and 8 mm wide overall, stigma 2-branched and twisted, each stigma 5 mm deep and 1.5 mm wide, Yellow 13A.
*Staminate flower*.—Grows to 3 cm deep and 8.1 cm wide, glabrous, inside Yellow 8B, bottom side Yellow 9D; 2 outer tepals, to 46 mm long and 40 mm wide, broadly obovate, margin entire to weakly undulate, tip obtuse, base obtuse; 2 inner tepals, to 44 mm long and 24 mm wide, obovate, margin entire, tip obtuse, base attenuate; stamen many in a globular head to 16 mm in long and 11 mm wide, filaments (on a column) 3 mm to 4 mm long, Green Yellow 1D, anthers 1 mm long and Yellow Orange 18A, pollen Yellow 8C.
*Fragrance*.—None.
*Lastingness*.—A cyme blooms for about 2 weeks on the plant, flowers are self-cleaning.

Fruit and seed: None seen.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

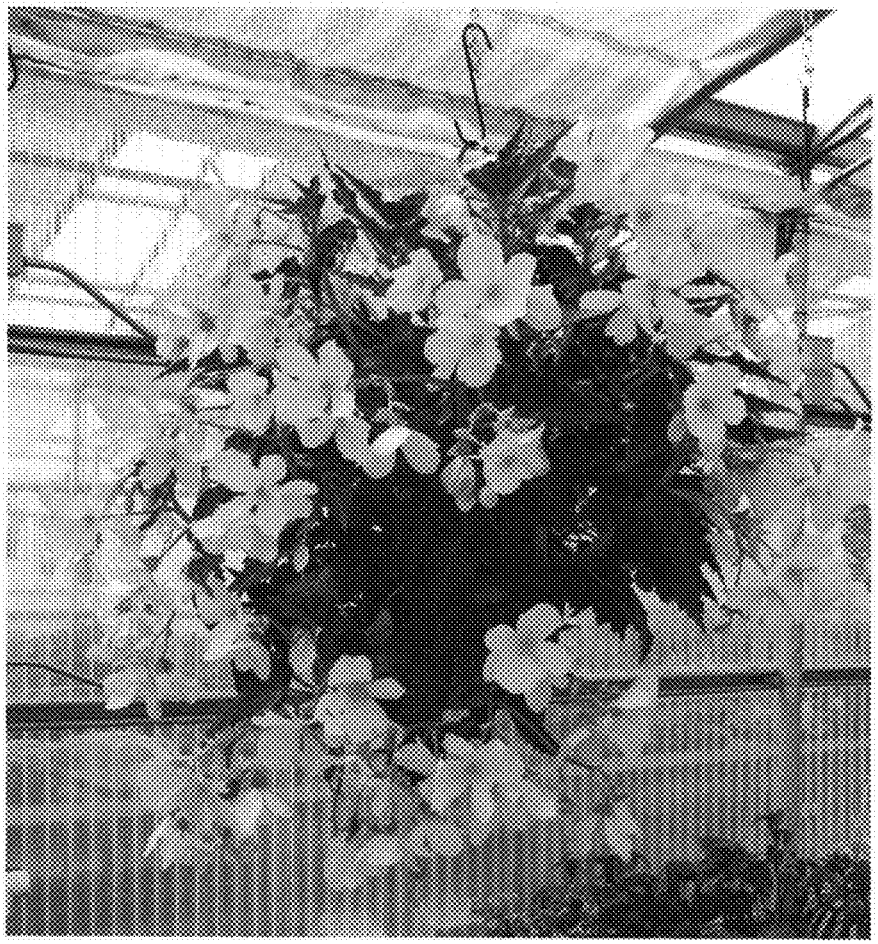
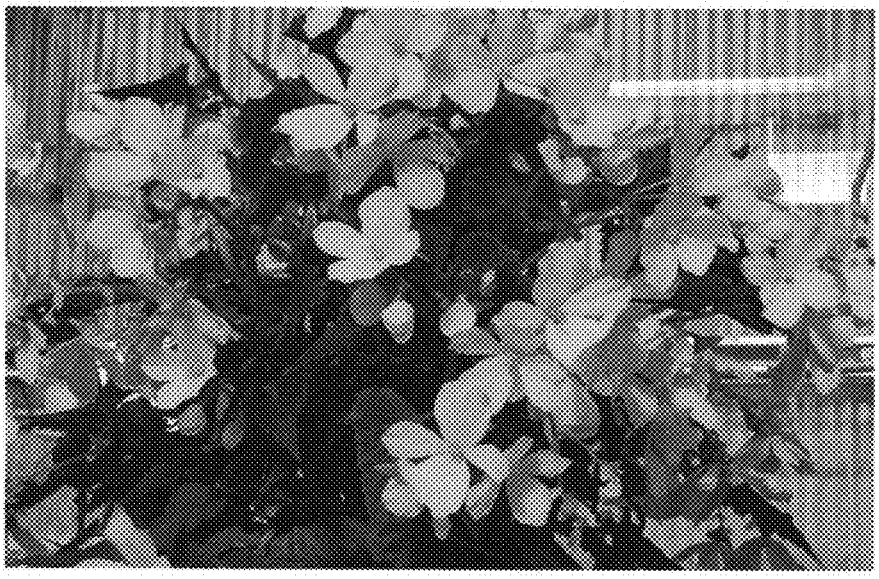
FIG. 1 top, FIG. 2 bottom